United States Patent
Single et al.

(10) Patent No.: US 12,048,564 B2
(45) Date of Patent: Jul. 30, 2024

(54) METHOD AND DEVICE FOR DETECTING A NEURAL RESPONSE IN A NEURAL MEASUREMENT

(71) Applicant: Saluda Medical Pty Ltd, Artarmon (AU)

(72) Inventors: Peter Scott Vallack Single, Artarmon (AU); Dean Michael Karantonis, Artarmon (AU)

(73) Assignee: Saluda Medical Pty Ltd, Macquarie Park (AU)

( * ) Notice: Subject to any disclaimer, the term of this patent is extended or adjusted under 35 U.S.C. 154(b) by 0 days.

(21) Appl. No.: 18/393,080

(22) Filed: Dec. 21, 2023

(65) Prior Publication Data
US 2024/0180496 A1   Jun. 6, 2024

Related U.S. Application Data (63) Continuation of application No. 17/716,545, filed on Apr. 8, 2022, now Pat. No. 11,890,113, which is a (Continued)

(30) Foreign Application Priority Data

Nov. 22, 2013   (AU) .................. 2013904519

(51) Int. Cl.
*A61B 5/00* (2006.01)
*A61B 5/24* (2021.01)
*A61N 1/36* (2006.01)

(52) U.S. Cl.
CPC .............. *A61B 5/7246* (2013.01); *A61B 5/24* (2021.01); *A61B 5/4848* (2013.01); (Continued)

(58) Field of Classification Search
CPC ........ A61B 5/7246; A61B 5/24; A61B 5/4848; A61B 5/6846; A61B 5/6877;
(Continued)

(56) References Cited

U.S. PATENT DOCUMENTS

| | | |
|---|---|---|
| 6,931,281 B2 | 8/2005 | Bradley et al. |
| 2004/0225211 A1 | 11/2004 | Gozani et al. |
| 2010/0249643 A1 | 9/2010 | Gozani et al. |

FOREIGN PATENT DOCUMENTS

| | | |
|---|---|---|
| WO | WO 2012/155185 A1 | 11/2012 |
| WO | WO 2012/155190 A1 | 11/2012 |

OTHER PUBLICATIONS

Franke, F. et al. "An Online Spike Detection and Spike Classification Algorithm Capable of Instantaneous Resolution of Overlapping Spikes," Journal of Computational Neuroscience, 2010, vol. 29, No. 1-2, pp. 127-148.

(Continued)

*Primary Examiner* — Patrick Fernandes
(74) *Attorney, Agent, or Firm* — Barnes & Thornburg LLP (57) ABSTRACT

A method for processing a neural measurement obtained in the presence of artifact, in order to detect whether a neural response is present in the neural measurement. A neural measurement is obtained from one or more sense electrodes. The neural measurement is correlated against a filter template, the filter template comprising at least three half cycles of an alternating waveform, amplitude modulated by a window. From an output of the correlating, it is determined whether a neural response is present in the neural measurement.

17 Claims, 9 Drawing Sheets

Related U.S. Application Data continuation of application No. 16/537,468, filed on Aug. 9, 2019, now Pat. No. 11,337,658, which is a continuation of application No. 15/037,038, filed as application No. PCT/AU2014/050369 on Nov. 22, 2014, now Pat. No. 10,426,409.

(52) U.S. Cl.
CPC .......... *A61B 5/6846* (2013.01); *A61B 5/6877* (2013.01); *A61B 5/7203* (2013.01); *A61B 5/7257* (2013.01); *A61N 1/36071* (2013.01); *A61N 1/36139* (2013.01); *A61B 5/7282* (2013.01); *A61B 2562/046* (2013.01); *G06F 2218/00* (2023.01)

(58) Field of Classification Search
CPC ... A61B 5/7203; A61B 5/7257; A61B 5/7282; A61B 2562/046; A61N 1/36071; A61N 1/36139; G06F 2218/00; G06K 9/00496
See application file for complete search history.

(56) References Cited

OTHER PUBLICATIONS

International Search Report and Written Opinion in PCT/AU2014/050369, dated Feb. 20, 2015, 14 pages.

METHOD AND DEVICE FOR DETECTING A NEURAL RESPONSE IN A NEURAL MEASUREMENT

CROSS-REFERENCE TO RELATED APPLICATIONS

This application is a continuation of U.S. patent application Ser. No. 17/716,545, filed Apr. 8, 2022, which is a continuation of Ser. No. 16/537,468, filed Aug. 9, 2019 and issued on May 24, 2022 as U.S. Pat. No. 11,337,658, which is a continuation of U.S. patent application Ser. No. 15/037,038, filed May 16, 2016 and issued on Oct. 1, 2019 as U.S. Pat. No. 10,426,409, which is a National Stage Application of International Application No. PCT/AU2014/050369, filed Nov. 22, 2014, which claims the benefit of Australian Provisional Patent Application No. 2013904519 filed 22 Nov. 2013. Each of these aforementioned applications is incorporated herein by reference in its entirety.

TECHNICAL FIELD

The present invention relates to detection of a neural response, such as a neural response caused by a stimulus. In particular the present invention relates to detection of a compound action potential by using one or more electrodes implanted proximal to the neural pathway to obtain a neural measurement.

BACKGROUND OF THE INVENTION

Electrical neuromodulation is used or envisaged for use to treat a variety of disorders including chronic pain, Parkinson's disease, and migraine, and to restore function such as hearing and motor function. A neuromodulation system applies an electrical pulse to neural tissue in order to generate a therapeutic effect. Such a system typically comprises an implanted electrical pulse generator, and a power source such as a battery that may be rechargeable by transcutaneous inductive transfer. An electrode array is connected to the pulse generator, and is positioned close to the neural pathway(s) of interest. An electrical pulse applied to the neural pathway by an electrode causes the depolarisation of neurons, which generates propagating action potentials whether antidromic, orthodromic, or both, to achieve the therapeutic effect.

When used to relieve chronic pain for example, the electrical pulse is applied to the dorsal column (DC) of the spinal cord and the electrode array is positioned in the dorsal epidural space. The dorsal column fibres being stimulated in this way inhibit the transmission of pain from that segment in the spinal cord to the brain.

In general, the electrical stimulus generated in a neuromodulation system triggers a neural action potential which then has either an inhibitory or excitatory effect. Inhibitory effects can be used to modulate an undesired process such as the transmission of pain, or excitatory effects can be used to cause a desired effect such as the contraction of a muscle or stimulation of the auditory nerve.

The action potentials generated among a large number of fibres sum to form a compound action potential (CAP). The CAP is the sum of responses from a large number of single fibre action potentials. When a CAP is electrically recorded, the measurement comprises the result of a large number of different fibres depolarising. The propagation velocity is determined largely by the fibre diameter and for large myelinated fibres as found in the dorsal root entry zone (DREZ) and nearby dorsal column the velocity can be over 60 ms$^{-1}$. The CAP generated from the firing of a group of similar fibres is measured as a positive peak $P_1$ in the recorded potential, then a negative peak $N_1$, followed by a second positive peak $P_2$. This is caused by the region of activation passing the recording electrode as the action potentials propagate along the individual fibres, producing the typical three-peaked response profile. Depending on stimulus polarity and the sense electrode configuration, the measured profile of some CAPs may be of reversed polarity, with two negative peaks and one positive peak.

Approaches proposed for obtaining a neural measurement are described by the present applicant in International Patent Publication No. WO 2012/155183, the content of which is incorporated herein by reference, and also by King (U.S. Pat. No. 5,913,882), Nygard (U.S. Pat. No. 5,758,651) and Daly (US Patent Application No. 2007/0225767), for example.

To better understand the effects of neuromodulation and/or other neural stimuli, and for example to provide a stimulator controlled by neural response feedback, it is desirable to accurately detect a CAP resulting from the stimulus. Evoked responses are less difficult to detect when they appear later in time than the artifact, or when the signal-to-noise ratio is sufficiently high. The artifact is often restricted to a time of 1-2 ms after the stimulus and so, provided the neural response is detected after this time window, a response measurement can be more easily obtained. This is the case in surgical monitoring where there are large distances (e.g. more than 12 cm for nerves conducting at 60 ms$^{-1}$) between the stimulating and recording electrodes so that the propagation time from the stimulus site to the recording electrodes exceeds 2 ms.

However to characterize the responses from the dorsal columns, high stimulation currents and close proximity between electrodes are required, and therefore in such situations the measurement process must overcome artifact directly. However, this can be a difficult task as an observed CAP signal component in the neural measurement will typically have a maximum amplitude in the range of microvolts. In contrast a stimulus applied to evoke the CAP is typically several volts and results in electrode artifact, which manifests in the neural measurement as a decaying output of several millivolts partly or wholly contemporaneously with the CAP signal, presenting a significant obstacle to isolating or even detecting the much smaller CAP signal of interest.

For example, to resolve a 10 uV CAP with 1 uV resolution in the presence of an input 5V stimulus, for example, requires an amplifier with a dynamic range of 134 dB, which is impractical in implant systems. As the neural response can be contemporaneous with the stimulus and/or the stimulus artefact, CAP measurements present a difficult challenge of measurement amplifier design. In practice, many non-ideal aspects of a circuit lead to artefact, and as these mostly have a decaying exponential appearance that can be of positive or negative polarity, their identification and elimination can be laborious.

The difficulty of this problem is further exacerbated when attempting to implement CAP detection in an implanted device. Typical implants have a power budget which permits a limited number, for example in the hundreds or low thousands, of processor instructions per stimulus, in order to maintain a desired battery lifetime. Accordingly, if a CAP detector for an implanted device is to be used regularly (e.g. once a second), then the detector should preferably consume only a small fraction of the power budget and thus desirably should require only in the tens of processor instructions in order to complete its task.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In this specification, a statement that an element may be "at least one of" a list of options is to be understood that the element may be any one of the listed options, or may be any combination of two or more of the listed options.

SUMMARY OF THE INVENTION

According to a first aspect the present invention provides a method for processing a neural measurement obtained in the presence of artifact, in order to detect whether a neural response is present in the neural measurement, the method comprising:

obtaining a neural measurement from one or more sense electrodes;

correlating the neural measurement against a filter template, the filter template comprising at least three half cycles of an alternating waveform, amplitude modulated by a window; and determining from an output of the correlating whether a neural response is present in the neural measurement.

According to a second aspect the present invention provides an implantable device for processing a neural measurement obtained in the presence of artifact, in order to detect whether a neural response is present in the neural measurement, the device comprising:

measurement circuitry for obtaining a neural measurement from one or more sense electrodes; and a processor configured to correlate the neural measurement against a filter template, the filter template comprising at least three half cycles of an alternating waveform, amplitude modulated by a window; and the processor further configured to determine from an output of the correlating whether a neural response is present in the neural measurement.

The window may comprise a triangular window. The triangular window may be a standard triangular window of length L comprising coefficients w(n) as follows:

For L odd:

$$w(n) = 2n/(L+1) \text{ for } 1 \le n \le (L+1)/2 = 2 - 2n(L+1) \text{ for } (L+1)/2 + 1 \le n \le L$$

For L even:

$$w(n) = (2n-1)/L \text{ for } 1 \le n \le L/2 = 2 - (2n-1)/L \text{ for } L/2 + 1 \le n \le L.$$

More preferably, the triangular window is a Bartlett window in which samples 1 and L are zero, and it is to be appreciated that the phrase triangular window herein is intended to encompass both a standard triangular window and a Bartlett window, as described above, as well as other substantially triangular or tent-shaped window functions. Alternatively, the window may comprise a Bartlett window, a Hanning window, a rectangular window or a Kaiser-Bessel window of suitable beta value.

In preferred embodiments of the invention, the filter template comprises four half-cycles of an alternating waveform. Such embodiments recognise that a matched filter, comprising a three-peaked template shaped somewhat like the expected three-peaked CAP response, used to correlate against an obtained neural measurement, can optimise SNR when the noise is white, but that artefact is not white noise and that such three-peaked matched filters may perform less optimally in CAP detection in the presence of artifact.

The filter template may comprise four half cycles of a sine wave, modified by being amplitude modulated by a triangular window, thus comprising four alternating peaks. Alternatively the filter template may comprise four half cycles of a cosine wave, modified by having an amplitude fitted within a triangular window, thus comprising five alternating peaks. Inverses of such filter templates, i.e. having opposite polarity, may be employed in some embodiments. The alternating waveform in alternative embodiments may be non-sinusoidal, but is preferably a continuous curve, and may in some embodiments resemble the profile of a neural response albeit comprising four half cycles.

The present invention thus provides for selection of a filter template having improved artifact rejection. The present invention recognises that artifact can be reasonably accurately modelled as a sum of two exponentials having distinct time constants, and that because a Bartlett filter template window rejects the first three terms of a Taylor expansion of et, namely the DC, linear, and quadratic terms, such embodiments of the present invention thus facilitate artifact rejection.

According to a third aspect the present invention provides a method for processing a neural measurement obtained in the presence of artifact, in order to detect whether a neural response is present in the neural measurement, the method comprising:

obtaining a neural measurement from one or more sense electrodes;

at a first time offset, correlating the neural measurement against a first filter template to produce a first measure $m_1$, the first filter template comprising an alternating waveform of a first phase;

at the first time offset, correlating the neural measurement against a second filter template to produce a second measure $m_2$, the second filter template comprising an alternating waveform of a second phase 90 degrees offset to the first phase;

at a second time offset, being at a non-integer multiple of 180 degrees offset from the first time offset, correlating the neural measurement against the first filter template to produce a third measure $m_3$;

at the second time offset, correlating the neural measurement against the second filter template to produce a fourth measure $m_4$; and processing $m_1$ to $m_4$ to detect whether a neural response exists in the neural measurement.

According to a fourth aspect the present invention provides a device for processing a neural measurement obtained in the presence of artifact, in order to detect whether a neural response is present in the neural measurement, the device comprising:

measurement circuitry for obtaining a neural measurement from one or more sense electrodes; and     a processor configured to:

at a first time offset, correlate the neural measurement against a first filter template to produce a first measure $m_1$, the first filter template comprising an alternating waveform of a first phase;

at the first time offset, correlate the neural measurement against a second filter template to produce a second measure $m_2$, the second filter template comprising an alternating waveform of a second phase 90 degrees offset to the first phase;

at a second time offset, being at a non-integer multiple of 180 degrees offset from the first time offset, correlate the neural measurement against the first filter template to produce a third measure $m_3$;

at the second time offset, correlate the neural measurement against the second filter template to produce a fourth measure m; and         process $m_1$ to $m_4$ to detect whether a neural response exists in the neural measurement.

In some embodiments of the third and fourth aspects the first filter template may be anti-symmetric so as to create an imaginary DFT output, while the second filter template may be symmetric so as to create a real DFT output.

In some embodiments of the third and fourth aspects the second time offset is offset by 90 degrees, or 270 degrees, from the first time offset.

In some embodiments of the third and fourth aspects the first and/or second filter template may each comprise four half cycles of an alternating waveform, amplitude modulated by a triangular window. For example the first filter template may comprise four half cycles of a sinusoid waveform amplitude modulated by a triangular window, and the second filter template may comprise four half cycles of a cosine waveform amplitude modulated by the triangular window. Alternatively, the alternating waveform of the first and second filter templates in some embodiments of the third and fourth aspects of the invention may be amplitude modulated by a Kaiser Bessel window, for example having $\beta=6$.

The first though fourth aspects of the present invention are further advantageous when applied in relation to an implanted device, in that performing a correlation of a filter template with a neural measurement typically requires only in the tens of processor instructions, and thus consumes a suitably small fraction of the power budget of a typical implant, as compared for example to a double exponential matched filter approach which would require hundreds of processor instructions. In preferred embodiments of the first though fourth aspects of the present invention only a single point of the correlation is calculated, at a predefined optimal time delay.

Some embodiments of the first through fourth aspects of the invention may provide a method for efficiently determining an optimum time delay when a signal to artifact ratio is greater than one, at which a first or single point of the cross-correlation between the neural measurement and the filter template should be produced, the method comprising:

at an approximate time delay between the neural response and the filter template, computing real and imaginary parts of the fundamental frequency of the DFT of the neural measurement;

calculating a phase defined by the real and imaginary parts;

relative to the fundamental frequency, calculating the time adjustment needed to change the calculated phase to pi/2; and     defining the optimum time delay as being the sum of the approximate time delay and the time adjustment.

Other embodiments of the third and fourth aspects of the invention may provide a method for efficiently determining an optimum time delay at which a first or single point of the cross-correlation between the neural measurement and the filter template should be produced, the method comprising:

at the first time offset, correlating the neural measurement against a third filter template to produce a fifth measure ms, the third filter template comprising an alternating waveform at double the frequency of the first filter template and of a third phase;

at the second time offset, correlating the neural measurement against the third filter template to produce a sixth measure $m_6$; and     determining from $m_5$ and me a decay in artefact between the first time offset and the second time offset.

The optimum time delay may then be used to define the single point at which the cross-correlation between the neural measurement and the filter template should be produced. The optimum time delay may be calculated regularly, for example prior to every attempted detection of a neural response, or occasionally, for example at one second intervals or in response to a detected change in the user's posture.

The fundamental frequency may be the frequency of the three phases of the CAP and/or may be the frequency of the four cycles of the filter template.

A length of the filter template is preferably selected so that the filter template comprises a number of filter points which, at a sampling rate at which the neural measurement is assessed, is four-thirds of the duration of a typical neural response.

In preferred embodiments the measurement is obtained in accordance with the teachings of International Patent Publication No. WO 2012/155183, by the present applicant. In further preferred embodiments the detector output is used in a closed loop feedback circuit to control neuromodulation, for example in conjunction with the techniques of International Patent Publication No. WO 2012/155188, by the present applicant, the content of which is incorporated herein by reference.

The present invention thus recognises that the amplitude of an evoked response can be measured by calculating the dot product of a neural measurement and a filter template, provided that the filter template is substantially orthogonal with the artefact and has a dot-product with the response which is close to that of a matched filter matched to the evoked response. The filter template preferably rejects DC, rejects first order signals (signals having a constant slope), and rejects low frequency signals which decay exponentially or similarly, such as artefact. The filter is preferably configured so as to be able to operate upon signals which occurred immediately after a stimulus.

While four lobes provides the optimal trade-off between rejection of artifact and noise gain, alternative embodiments of the present invention may usefully employ a filter template comprising greater or fewer lobes. In such embodiments the filter template may comprise one or more basis functions derived from a sinusoidal binomial transform (SBT), for example. In embodiments comprising a three or five lobed filter template the window preferably comprises a flat central portion, as returned by the SBT, rather than a triangular peak for example, in order to better reject DC and ramp components of a Taylor expansion and thus better reject artifact. Some embodiments of the invention may use multiple identical filter template elements, but shifted in time. Even though these are not orthogonal, a successive approximation method creating a compound template may provide better approximation. Additionally or alternatively, some embodiments may use templates that are a sum of templates of different frequencies, templates of different offset and/or templates of different numbers of lobes.

BRIEF DESCRIPTION OF THE DRAWINGS

An example of the invention will now be described with reference to the accompanying drawings, in which:

FIG. 3b illustrates a modified version of the embodiment of FIG. 3a;

DESCRIPTION OF THE PREFERRED EMBODIMENTS

Figure 1:
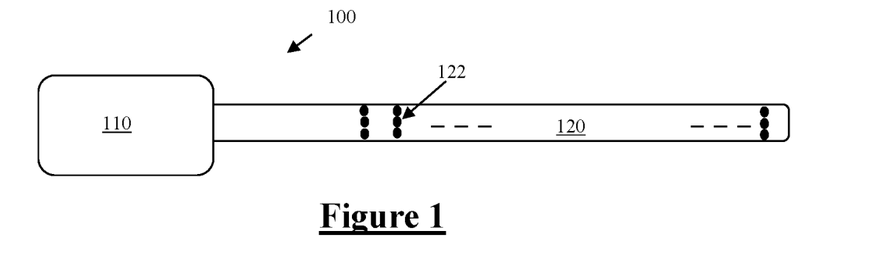
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. The control unit 110 includes a storage memory (or other storage device(s), not shown) for storing a lookup table that contains data defining a therapy map, setting out a relationship between applied stimuli regimes and the desired neural response. Device 100 further comprises an electrode array 120 consisting of a three by eight array of electrodes 122, each of which may be selectively used as either the stimulus electrode or sense electrode, or both.

Figure 2:
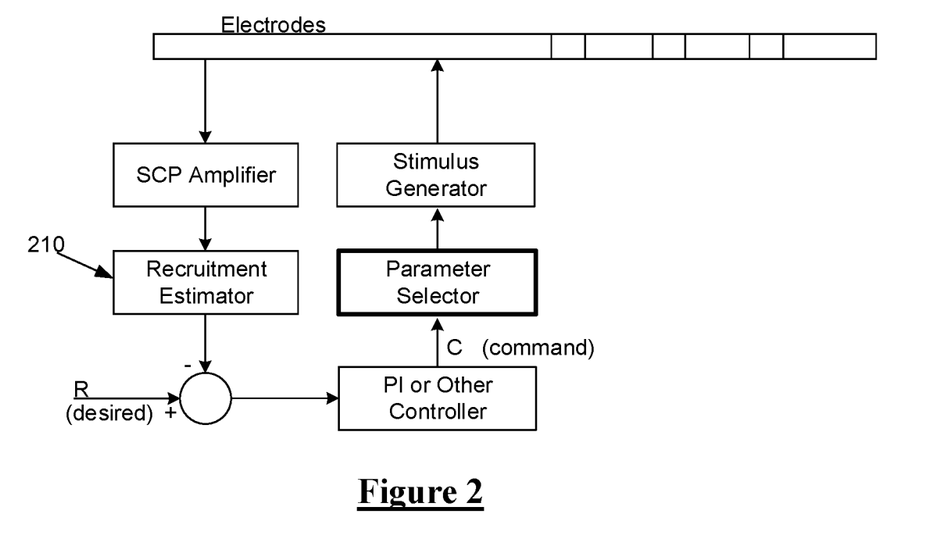
FIG. 2 is a schematic of a feedback controller to effect stimulus control in response to recruitment.

FIG. 2 is a schematic of a feedback controller implemented by the control unit 110, based on recruitment. An important component of such feedback control is a recruitment estimator 210, which is tasked with the difficult operation of, in a simple form, detecting whether a neural response is present in a neural measurement output by the spinal cord potential (SCP) amplifier, or in a more complex form determining an amplitude of any such neural response.

The evoked CAP measurements in this embodiment are made by use of the neural response measurement techniques set out in International Patent Publication No. WO2012/155183.

Figure 3A:
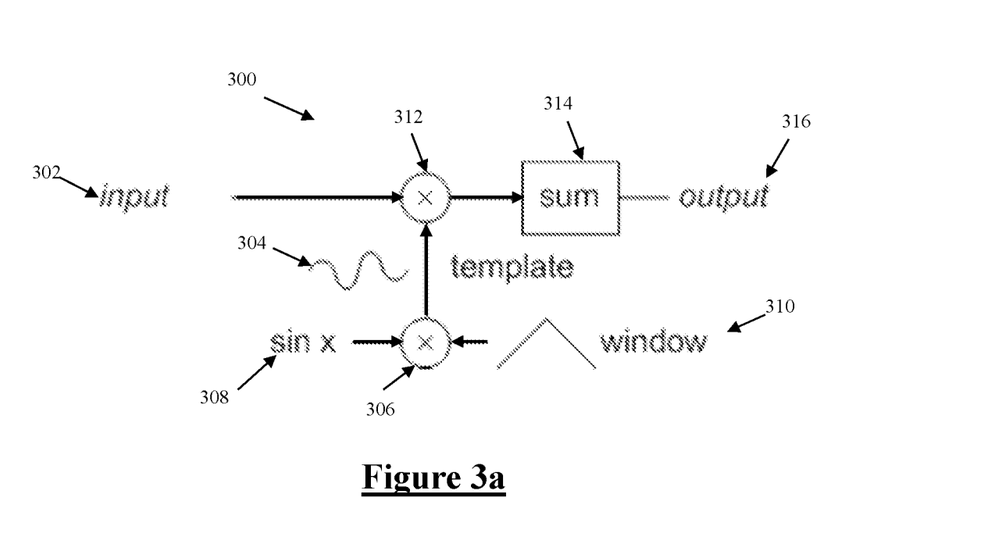
FIG. 3a illustrates a neural response detector in accordance with one embodiment of the invention.
Figure 3B:
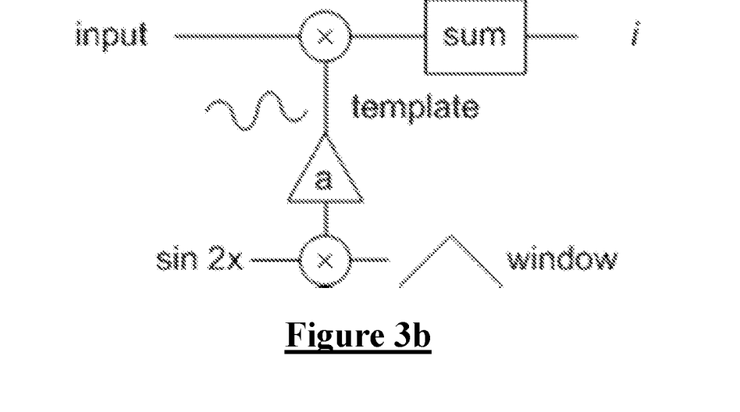

FIG. 3a illustrates a neural response detector 300 in accordance with one embodiment of the invention. A digitised sampled form of the neural measurement obtained by the SCP amplifier is taken as the input 302. A filter template 304 is created at 306 by modulating a sine wave 308 with a Bartlett window 310. In alternative embodiments the template is likely to be predefined in this manner and simply retrieved from a memory or the like within control unit 110. A dot product of a suitable window of the neural measurement 302 and the filter template 304 is calculated at 312, 314, to produce the detector output 316, which is a single value scalar. The detector 300 may be modified as shown in FIG. 3b by the addition of a gain term "a" for example to allow the correlator to produce approximately the same result as a peak-to-peak ECAP detector for comparison.

Figure 4:
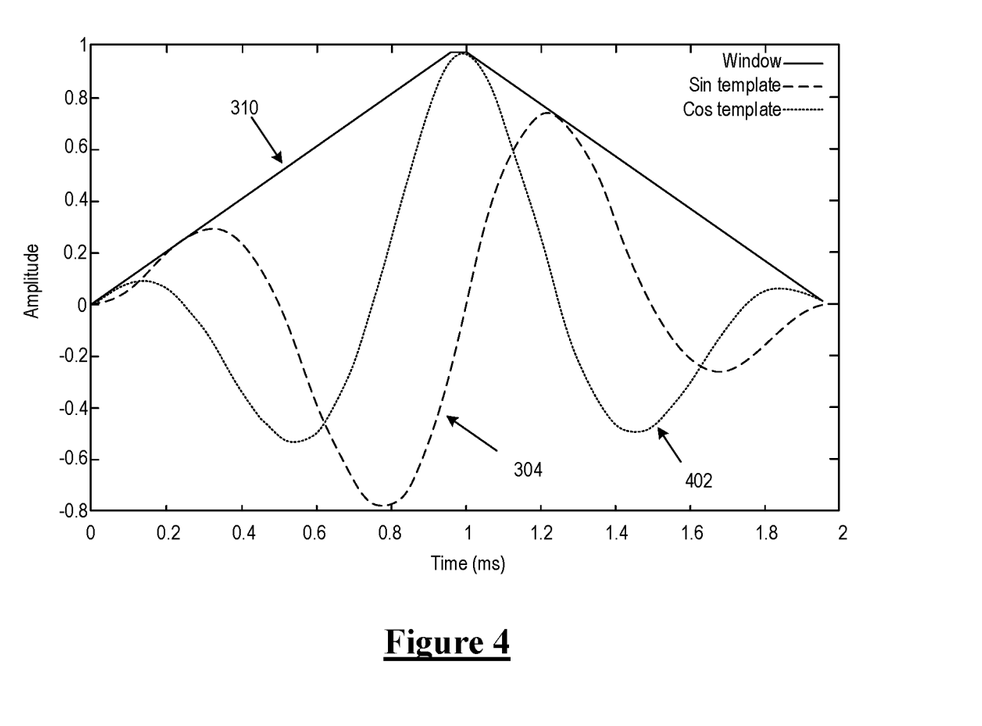
FIG. 4 illustrates the amplitude profile of the filter template used in the detector of FIG. 3; and a cosine filter template, and the Bartlett window.

FIG. 4 illustrates the amplitude profile of the filter template 304 used in the detector 300 of FIG. 3. FIG. 4 further illustrates the Bartlett window 310 used to amplitude modulate the sine wave 308. To assist in the following discussion, FIG. 4 also shows an additional filter template 402, comprising a cosine wave amplitude modulated by the Bartlett window 310. It is noted on the x-axis of FIG. 4 that the filter templates 304 and 402 each comprise a sufficient number of points such that at the sampling rate used the filter templates each cover a time period of almost 2 ms, which is four-thirds of the duration of an expected neural response in this embodiment.

Figure 5A:
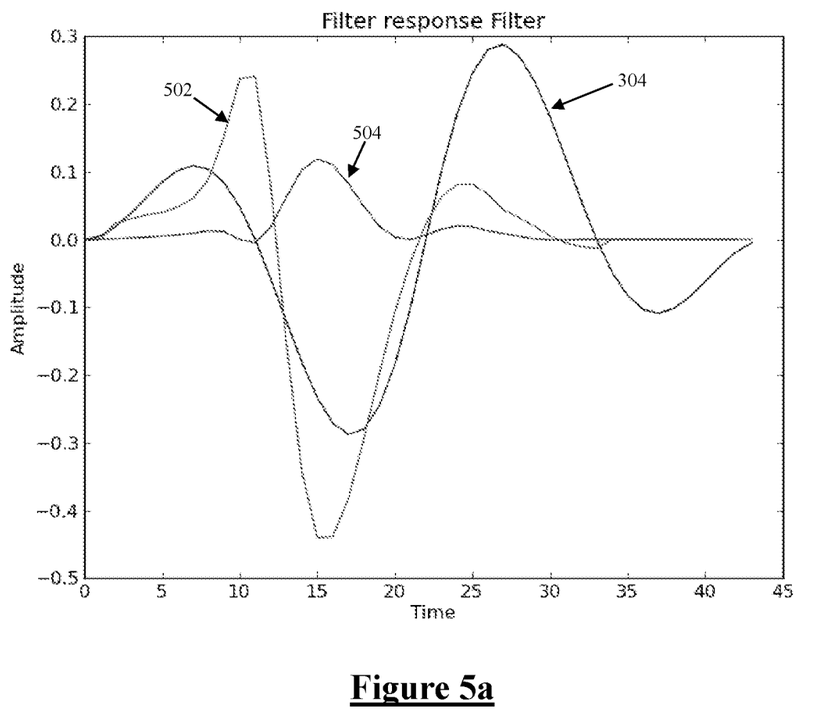
FIG. 5a illustrates the ability of the filter template to pass an evoked response.
Figure 5B:
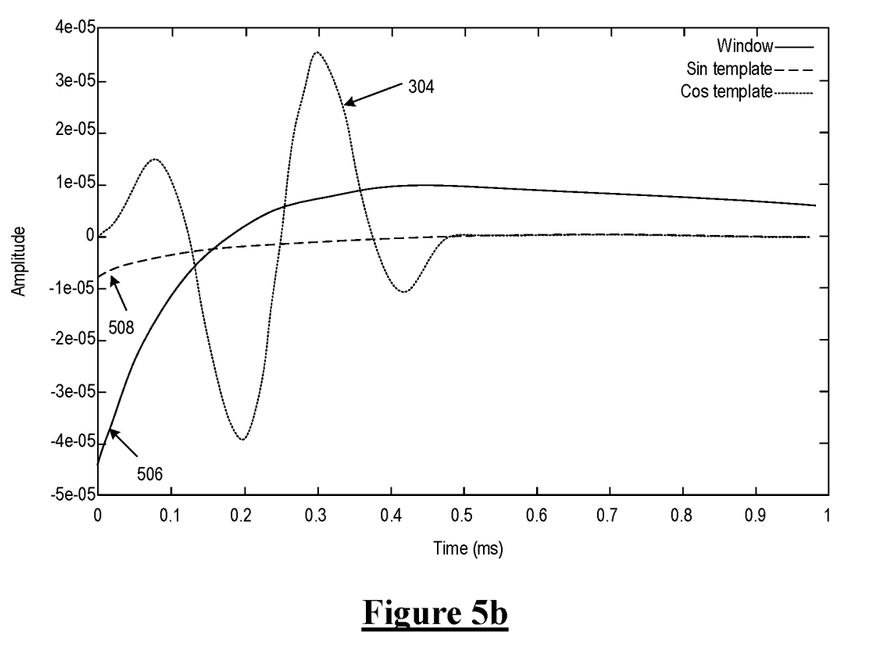
FIG. 5b illustrates the ability of the filter template to block artefact.

FIG. 5a illustrates an evoked response 502 in the absence of artefact, the four-lobe filter template 304, and the sliding dot product or cross correlation thereof, 504. Again, it is noted that the response 502 comprises three lobes, whereas the filter template 304 comprises four lobes and is four-thirds the expected length of the response 502. As can be seen in the sliding dot product 504, the evoked response 502 is substantially passed to the output of the detector 300 by the filter template 304. In contrast FIG. 5b illustrates the correlation 508 of the four lobe filter template 304 with pure artefact 506, illustrating that artefact is substantially blocked or heavily attenuated by the filter template 304 and thus not passed to the output of the detector 300. In this embodiment, the performance of the four-lobe filter template 304 at passing an expected neural response is within 2 dB of that of a matched filter, but with significantly improved artifact rejection.

It is noted that when sampling at 10 kHz, for example, 20 samples will be obtained in a 2 ms window, so that to determine the entire cross correlation will require 400 multiply/add operations. Accordingly, rather than calculating the entire cross-correlation between a measured neural response and the filter template, the present embodiment further provides for calculation of only a single point of the correlation as the output 316 of detector 300, as a single point requires only 20 samples when sampling a 2 ms window at 10 kHz. Noting that the arrival time of the neural response, or its position within the neural measurement 302, is not known a priori, it is necessary to determine an optimal time delay or offset between the neural measurement and the template filter, at which the single point of the correlation should then be calculated. The aim is to calculate the single point at the peak of the curve 504, and no other. To this end, the present embodiment efficiently determines the optimal time delay, by noting the following.

The DFT is defined by:

$$X_k = \sum_{n=0}^{N-1} x_n \cdot e^{-i2\pi kn/N} \quad (1)$$

In equation (1), and in the rest of this document, frequency-domain signals are represented by capital letters, and time-domain signals using lower-case. When using the DFT for spectral analysis, it is usual to multiply the data by a window W(n) so this becomes:

$$X'_k = \sum_{n=0}^{N-1} x_n \cdot W(n) \cdot e^{-i2\pi kn/N} \quad (2)$$

This can be expressed in traditional magnitude and phase terms where the magnitude of the windowed DFT term is $$|X'_k| = \sqrt{\text{Re}(X'_k)^2 + \text{Im}(X'_k)^2} \quad (3)$$

and the phase of the windowed DFT term is $$\Phi'_k = \tan^{-1}\left(\frac{\text{Re}(V'_k)}{\text{Im}(V'_k)}\right) \quad (4)$$

Figure 6:
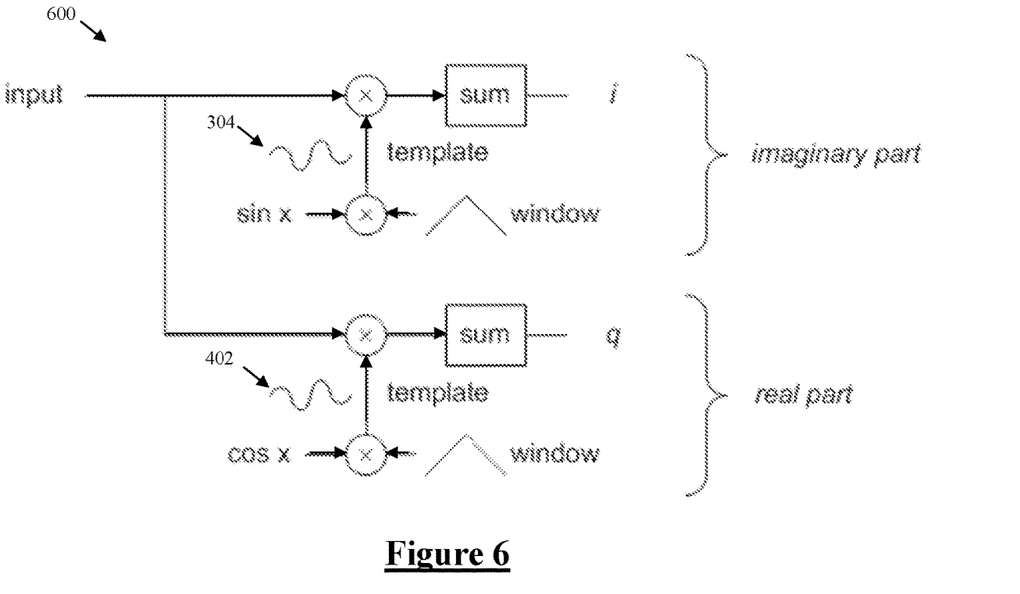
FIG. 6 illustrates hardware to compute a complex term of the windowed DFT.

The hardware 600 used to compute one term of $X'_k$ is illustrated in FIG. 6. Notably, the sine template 304 and cosine template 402 shown in FIG. 4 are used in the circuit 600. Comparing this arrangement to the previous equation, for which the third term is:

$$X'_2 = \sum_{n=0}^{N-1} x_n \cdot W(n) \cdot e^{-i4\pi n/N}, \quad (5)$$

it is noted that detector 300 using the filter template 304 (FIG. 3) computes the imaginary part of the third term of the windowed DFT. Thus, references to the output of the detector 300 are to be understood as being the imaginary part of the third term of the windowed DFT, and this is important to an understanding of the following further refinements of the invention.

Figure 7A:
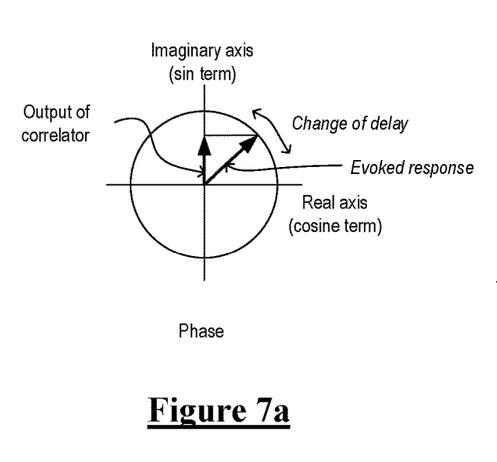
FIGS. 7a and 7b illustrate the effect of a clinical fitting procedure of the evoked response detector.
Figure 7B:
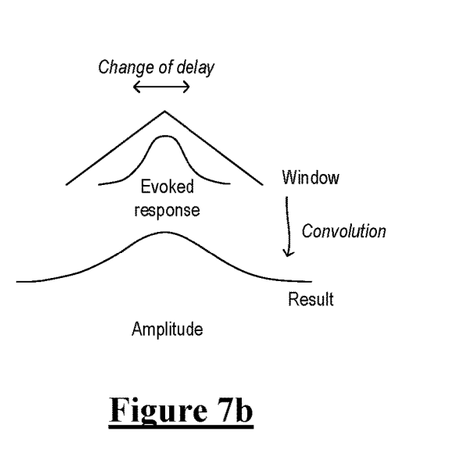

This also provides insight into what happens as the time delay is adjusted during a clinical fitting procedure, as shown in FIGS. 7a and 7b. While FIG. 7b shows a triangular window and a single lobed response, this is for simplicity of representation and is intended to represent the four lobed filter template 304 and the three lobed response 502, respectively. Exploring different time delay adjustments by sliding the offset or delay in the time domain (FIG. 7b), rotates the coordinate system of the measurement (FIG. 7a). When the evoked response phase aligns with the imaginary axis of FIG. 7a, the output of the detector 300 is at its maximum. This also presents a computationally efficient solution to the problem when at this phase; when the correlator output is maximum, the real part of the spectral component is zero, so its calculation can be avoided as depicted in FIG. 3, saving processor cycles. The output of the detector 300 is the projection of the (complex) evoked response onto the imaginary axis.

When considering the entire cross correlation as the evoked response slides across the window (FIG. 7b), the evoked response vector in FIG. 7a rotates a full 360 degrees around the origin at least twice, and thus changes relatively quickly. However as shown at the bottom of FIG. 7b, the amplitude of the convolution of the evoked response and the window changes relatively slowly. Accordingly, the present embodiment recognises that a swift technique to align the evoked response with the imaginary axis and thus find the peak in the correlator output is to:
1. Roughly align the window and the signal S(t);
2. Calculate the imaginary (sin) and real (cosine) terms:
   a. I=S(t)·W(t)·sin(1 KHz·2π·t), and
   b. Q=S(t)·W(t)·cos(1 KHz·2π·t);
3. Find the angle to the y-axis using atan(Q/I);
4. As the template has fixed known frequency, calculate the time shift needed to set the sin term to its maximum;
5. Calculate the imaginary (sin) and real (cosine) terms for the new delay. The cosine term should be much smaller than the sin term confirming that the method worked.

Such embodiments may be particularly advantageous as compared to a clinical process requiring exploration of the varying delays in order to find a peak The present embodiment further incorporates the third and fourth aspects of the invention, and recognises that the artifact 506 can be well modelled as being a sum of two exponentials, of differing time constant. Each exponential component has a voltage and a time value, leading to $$a(t) = v_1 \exp\left(\frac{-t}{\tau_1}\right) + v_2 \exp\left(\frac{-t}{\tau_2}\right) \quad (6)$$

where $v_i$ and $\tau_i$ are constants for each component.

If $$e(t) = v\exp(-t/\tau) \quad (7)$$

then we can consider its windowed DFT $E'_k$, for which each term will have a magnitude and phase, and the term $E'_2$ can be calculated with the complex correlator 600 of FIG. 6.

If we take some signal $e^{-t/\tau}$ and shift the point in the signal at which the correlation is performed by some arbitrary time T, since $$e^{-(t+T)/\tau} = e^{-t/\tau} e^{-T/\tau}$$

$$e^{-(t+T)/\tau} = c \cdot e^{-t/\tau} \quad (8)$$

where c is some constant.

Figure 8:
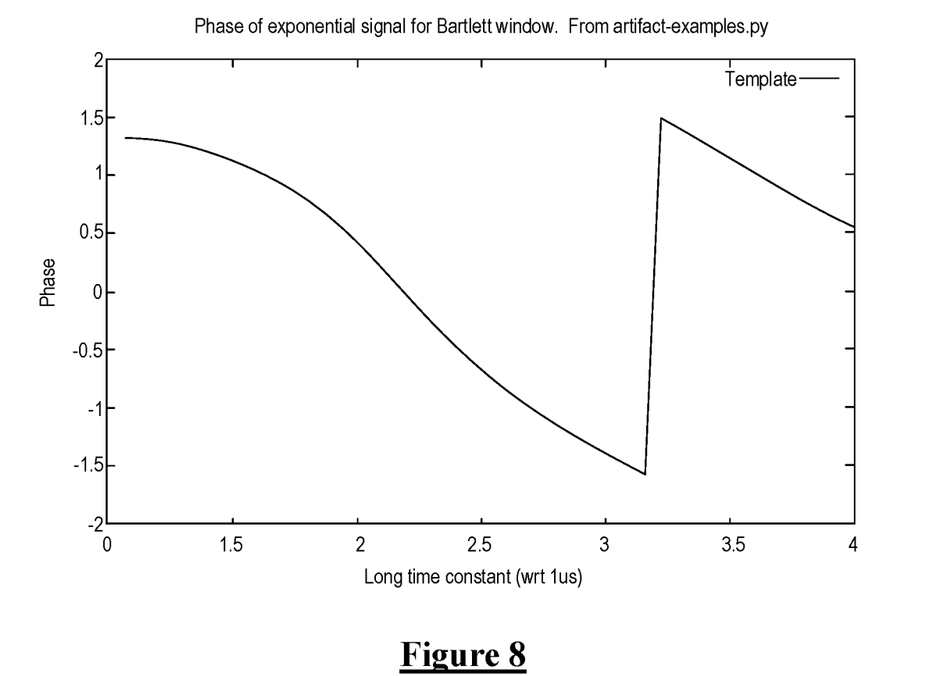
FIG. 8 illustrates the dependency of the phase of the DFT terms of an exponential on the time constant of the exponential.

Thus, the phase of the DFT terms of a single exponential depend on the time constant of the exponential, as shown in FIG. 8 for the filter template 304. However, the present embodiment recognises that the phase of each DFT term is unchanged by time delay.

Figure 9A:
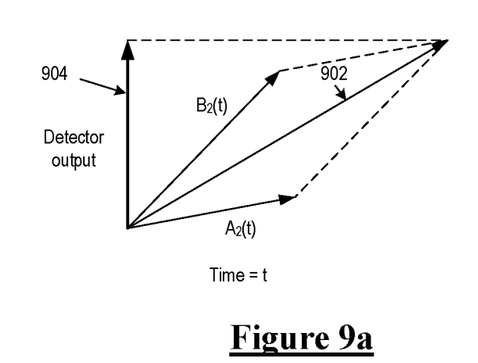
FIGS. 9a and 9b illustrate, at respective times, the detector output vector components arising from artefact only, when modelled as two exponentials.
Figure 9B:
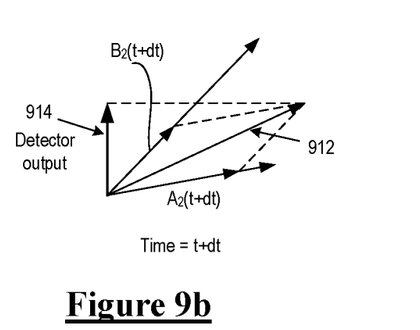

FIG. 9 illustrates the filter output vector components arising from artefact only, when modelled as two exponentials. At a first time, shown in FIG. 9a, $A_2$ and $B_2$ are the two artifact phase vectors. These can be added using vector addition to produce the total artefact 902. The detector 300 will thus produce an output 904 which is the imaginary part of this vector; the projection of 902 onto the y-axis. As time passes, the lengths of the two vectors reduce exponentially, but at different rates as the time constants are different, $B_2$ decaying rapidly and A2 decaying slowly. However, the phases remain unchanged as per equation (8), resulting in the situation shown in FIG. 9b. The total artefact vector is now 912, which due to the different relative contributions from each exponential component is of slightly changed phase to 902. The detector 300 will thus produce an output 914.

Figure 10A:
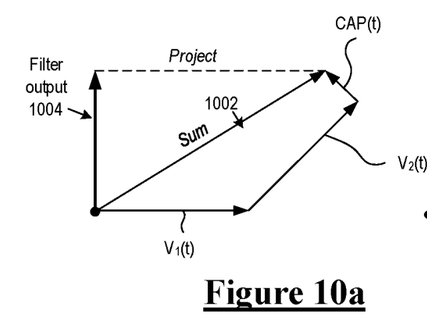
FIGS. 10a and 10b illustrate, at respective times, the detector output vector components arising from artefact modelled as two exponentials and from an evoked response.
Figure 10B:
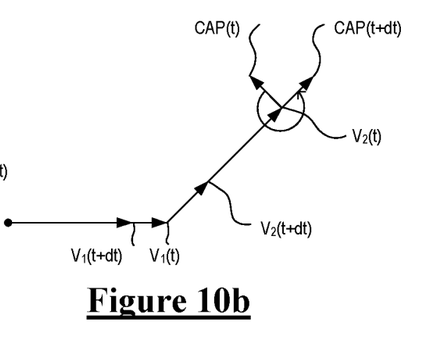

FIGS. 10a and 10b illustrate, at respective times, the detector output vector components arising from artefact modelled as two exponentials and from an evoked response. At a first time t, shown in FIG. 10a, $V_1$ and $V_2$ are the two artifact phase vectors, and CAP is the evoked response vector. These can be added using vector addition to produce the total artefact 1002. The detector 300 will thus produce an output 1004 which is the imaginary part of this vector; the projection of 1002 onto the y-axis. At a later time t+dt, the lengths of the two artefact vectors have reduced exponentially, at different rates as the time constants are different, with $V_2$ decaying rapidly and $V_1$ decaying slowly. However, the phases remain unchanged as per equation (8), as shown in FIG. 10b. In contrast, the amplitude of the evoked response vector CAP changes relatively slowly as discussed in relation to FIG. 7b, but undergoes a change in phase as discussed in relation to FIG. 7a. Thus, as shown in FIG. 10b, the CAP vector rotates without undergoing a significant amplitude change. Thus, at one moment (FIG. 10a) the CAP vector can be orthogonal to $V_2$, and at a later time (FIG. 10b) can be aligned with $V_2$.

When modelling the artefact as a sum of two exponential terms, it has been determined from measurements of actual artefact that the time constant $\tau_1$ of the first (slow) exponential term is typically in the range 300 us to 30 ms, more typically 500 μs to 3 ms and most commonly about 1 ms, and that the time constant $\tau_2$ of the second (fast) exponential term is typically in the range 60-500 μs, more typically 100-300 μs, and most commonly about 150 μs.

Figure 11A:
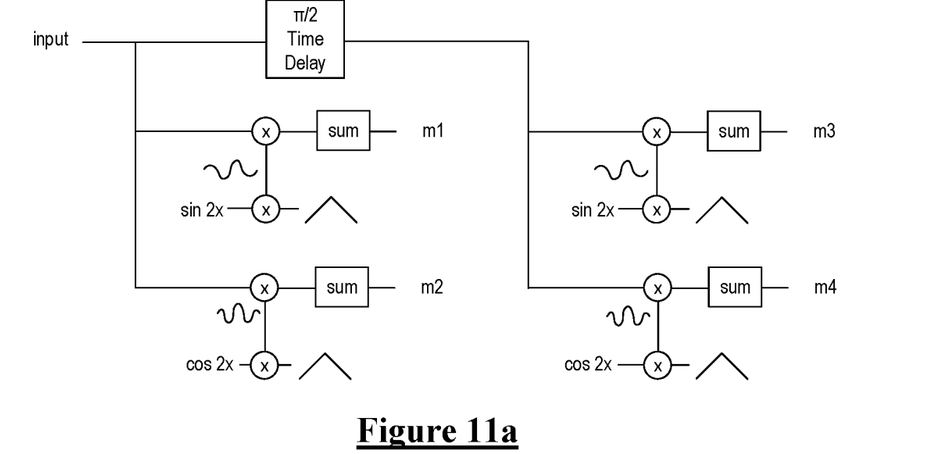
FIGS. 11a and 11b illustrate a four point measurement technique for measuring a CAP.

The method of this embodiment, utilising the third and fourth aspects of the invention, relies on making two complex measurements of the evoked response, at points in time separated by one quarter of a cycle, as shown in FIG. 11a. The timing of the measurements is optimised in the manner described above in relation to FIGS. 7a and 7b, so that the first measurement ($m_1$ and $m_2$) has a purely imaginary evoked response contribution (i.e. the evoked response aligns with the sin correlator 304), and the second measurement (m3 and m4) is purely real (i.e. aligns with the cosine 402). This leads to four measurements, m1 to m4. There are four unknowns—the magnitude of the artifact, the magnitude of the evoked response, the phase of the artifact and the time constant of the fast exponential. The slow exponential component of the artifact is well rejected by the filter template 304 and thus can be omitted. It is known that the artifact contribution to the sin and cos correlators has a fixed ratio. Using simple algebra the unknowns can be eliminated. Therefore any CAP present in the neural measurement can be calculated as being:

$$CAP = m_4 - k \cdot m_2 \quad (9)$$

Where $$k = \frac{m4 - m1 \pm \sqrt{(m4 - m1)^2 + 4 \cdot m2 \cdot m3}}{2 \cdot m2} \quad (10)$$

Figure 11B:
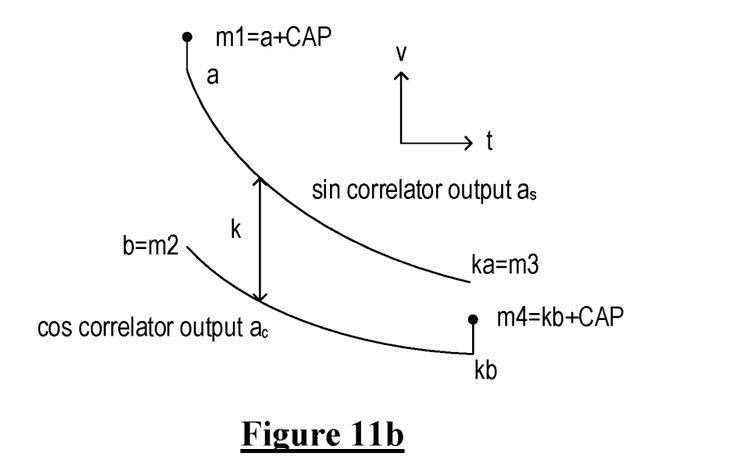

FIG. 11b illustrates the locations of these four measurements $m_1$ to $m_4$ on the real and imaginary detector outputs.

Knowing k also allows the evaluation of t, and of the fast artifact exponential:

$$\tau = \frac{-T}{\ln(k)} \quad (11)$$

To find the voltage of the fast exponential term for the artifact, one can further calculate the DFT of the exponential which is what would be expected from the detectors for an exponential input of that time constant, normalized to 1.0:

$$X_2' = \sum_{n=0}^{N-1} e^{\frac{-t}{\tau}} \cdot W(n) \cdot e^{-i 4\pi n / N} \quad (12)$$

Then, an estimation of the fast artifact term is:

$$A(t) = \frac{e^{-t/\tau}}{X_2'} \quad (13)$$

Figure 12:
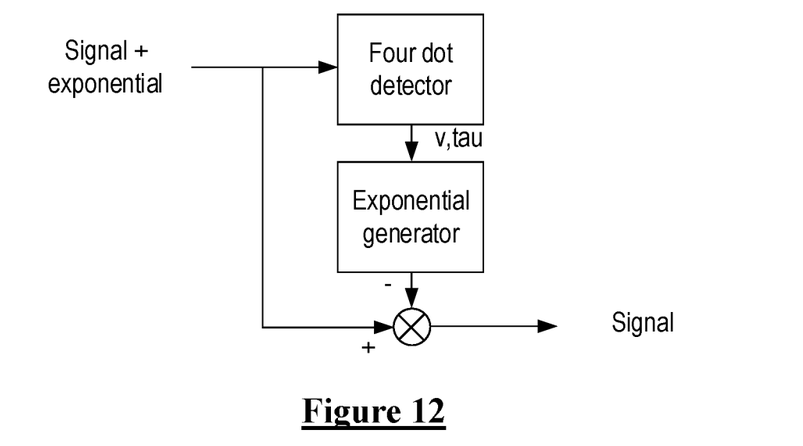
FIG. 12 illustrates exponential estimation and subtraction.

Having calculated the above, it is possible to improve the SAR of the signal by subtracting the estimated exponential, as shown in FIG. 12.

A difficulty in implementing this algorithm with measured data is that it measures two signals at once, namely the evoked response and the fast exponential, and each forms a noise source for the other. Usually, the phase of the evoked response is not known exactly, and this introduces errors into FIG. 11b. When the evoked response is larger than the exponential, and the phase of the evoked response is not known, the exponential estimation algorithm does not always find a solution, so the present embodiment further provides a second estimation method for these circumstances. This further estimation method recognises that the above algorithms can be extended by adding an additional correlation, to allow the phase of the evoked response to be calculated instead of being used as an input.

Figure 13:
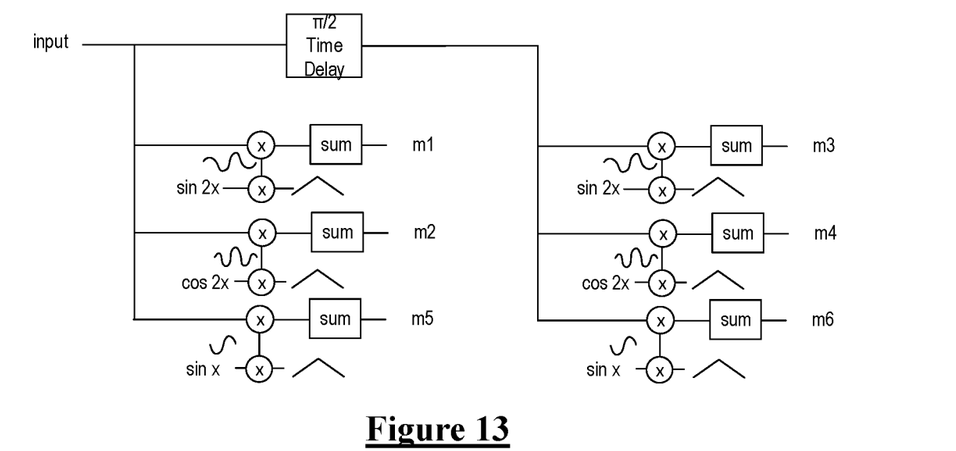
FIG. 13 illustrates a system for 6 point detection for when relative phase between evoked response and sampling window is unknown.

When the relative phase (θ) of the evoked response to the sampling window is unknown, the proposal of FIG. 11 has 5 unknowns and 4 measurements, so the unknowns cannot be found. By adding two more DFT points this can be overcome, as shown in FIG. 13. These additional points (m5 and m6) are evaluated at a frequency equal to half the fundamental of the evoked response—to which the evoked response is orthogonal. Therefore these two additional points allow k to be evaluated:

$$k = \frac{m6}{m5} \quad (14)$$

In turn, the five terms a, b, k, θ and c can be found. For some phase θ between the measurement window and the evoked response:

m1=a+c sin θ m2=b+c cos θ m3=ak+c cos θ m4=bk+c sin θ (15)

so:

$$a = \frac{(m1 - m4) + k(m2 - m3)}{1 - k^2} \quad (16)$$

$$b = m2 - m3 + ak \quad (17)$$

$$c = \sqrt{(m1-a)^2 + (m2-b)^2} \quad (18)$$

$$\theta = \sin^{-1}\left(\frac{m1-a}{c}\right) \quad (19)$$

The phase will change slowly, so once θ is known, it is possible to adjust the delay of the sampling window, and then revert to the four point algorithm of FIG. 11.

When considering implementation of the six point technique of FIG. 13, it is noted that in some embodiments an FFT will compute this faster than a DFT, especially if the FFT is factored to use the smallest number of multiply operations. A good choice of DFT length might be 16, factored as $(F_2 \cdot F_2) \cdot (F_2 \cdot F_2)$. For this factorization the twiddle factors between the F operations are trivial, and so the only complex multiply required is in the middle.

Figure 14:
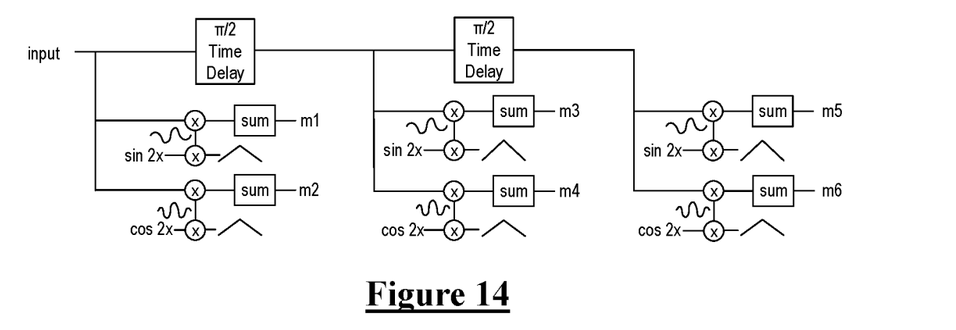
FIG. 14 illustrates an alternative embodiment for 6-point detection.

FIG. 14 illustrates an alternative embodiment utilising six measurement points.

It is further noted that running the calculation after the evoked response is finished allows the slow exponential to be measured.

The evoked response in the spine (having three phases) takes approximately 1 ms. In embodiments employing a sample rate of 30 KHz or a simple interval of 33 us, the evoked response will take around 30 samples. Consequently in such embodiments the filter template having four phases will comprise approximately 40 tap values, or data points. In alternative embodiments, using an alternative sampling rate or measuring a faster or slower CAP, the length of the filter may comprise correspondingly greater or fewer filter taps.

While the preceding embodiments have been described in relation to a filter template which comprises four half cycles, alternative embodiments of the present invention may nevertheless usefully employ a filter template comprising greater or fewer lobes. The present invention thus recognises that the ideal number if lobes is four. This is in contrast to a two lobe filter, which will have equal first and second lobes and will thus put more emphasis on the early parts of the signal where the signal-to-artifact is worse. Further, a filter with an odd number of lobes does not tend to have good artifact rejection properties. Moreover, if one were to use a six-lobe filter, or higher even-number lobed filter, the window becomes too wide relative to the 3-lobed neural response, and at least half the correlation time would just be looking at noise. Since most of the problematic artifact is in the first two lobes, a 6 lobe filter will tend not to provide better artifact rejection than the four-lobe filter. Four lobes thus provides the optimal trade-off between rejection of artifact and noise gain.

Figure 15A:
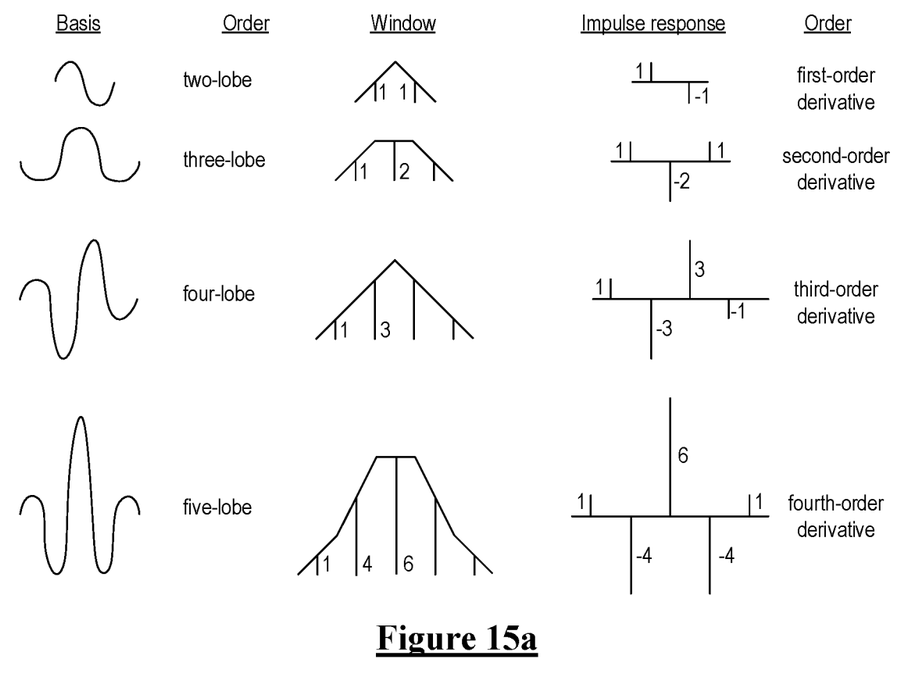
FIGS. 15a and 15b illustrates generation of filter templates having three, four and five lobes, respectively.
Figure 15B:
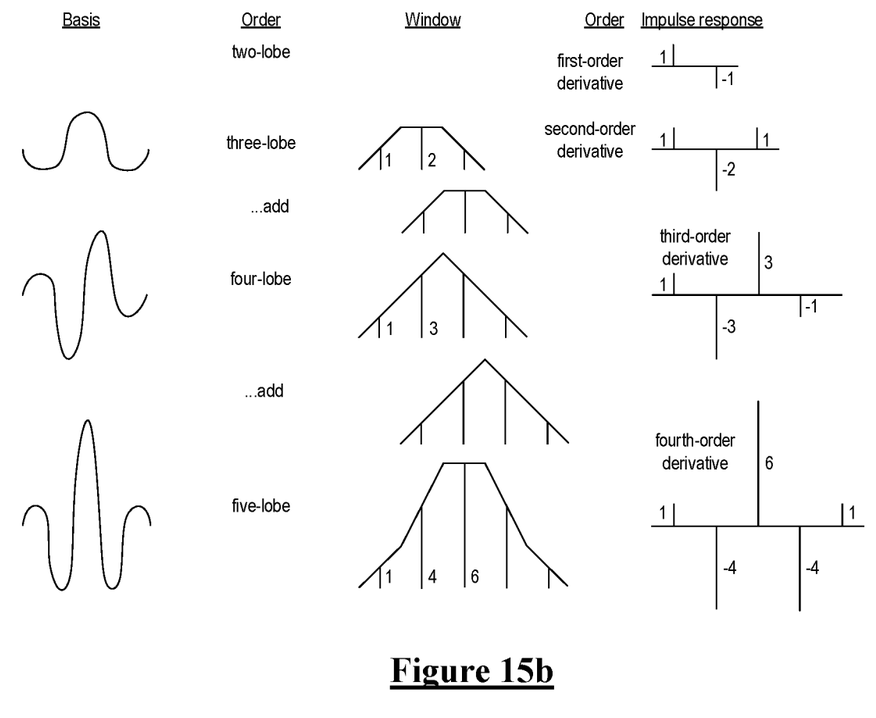

Nevertheless, alternative embodiments of the present invention may usefully employ a filter template comprising greater or fewer lobes. We now describe the mathematical properties of templates of other embodiments of the invention. The term "template" is used to refer to a filter used via correlation to detect an ECAP. A template may be comprised of one or more wavelets or basis functions, or may be derived by some other method, and is configured to preferentially pass an ECAP but preferentially block or be orthogonal to artifact. FIG. 15a illustrates sinusoidal binomial vectors in accordance with further embodiments of the invention. FIG. 15b shows the generation of three-lobe, four-lobe and five-lobe templates. A notable property of the SBT is that its basis functions of the same length are orthogonal. It is to be appreciated that the method used to generate the templates of FIG. 15 up to five-lobes can be extended to a greater number of lobes. It is further noted that the window is not triangular for three or five lobed filter templates, but has a flat central portion in both cases, and in the case of five lobes the window having a piecewise linear rise and fall. Thus, the three lobed filter template window proposed by the present embodiments is not triangular but is a flat topped window, which has been found to significantly improve artefact rejection as compared to a triangular window of a three lobed filter template.

That is, an important property of the sinusoidal binomial transform (SBT) is its ability to reject polynomial signals. If an SBT template of order n is used, it will reject all the terms of the Taylor series up to order n.

Figure 16A:
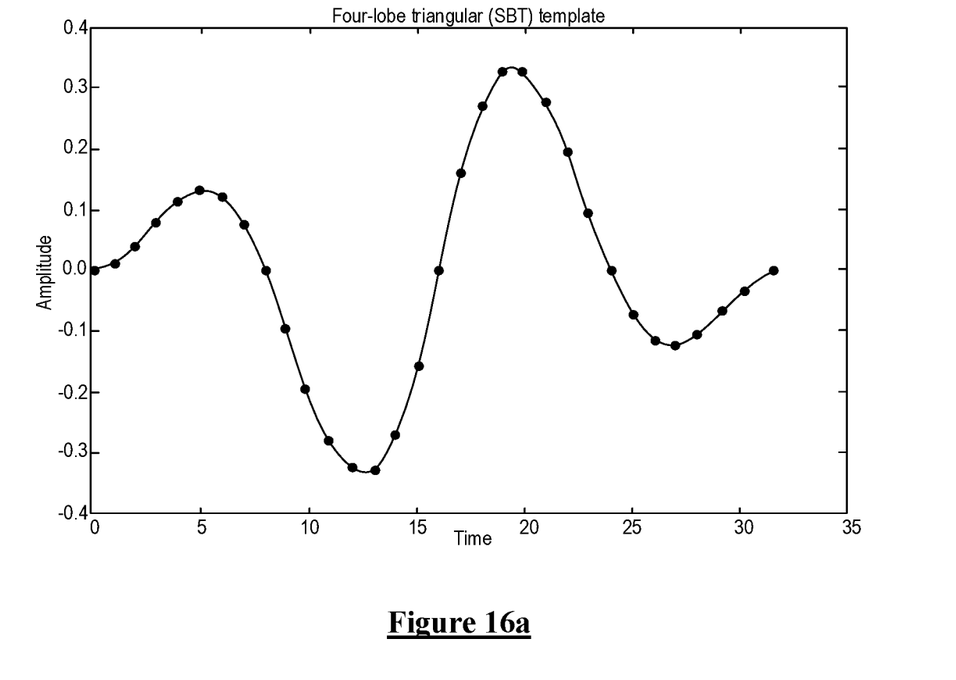
FIGS. 16a and 16b respectively illustrate four and three lobed filter template point values, derived from the approach of FIG. 15.
Figure 16B:
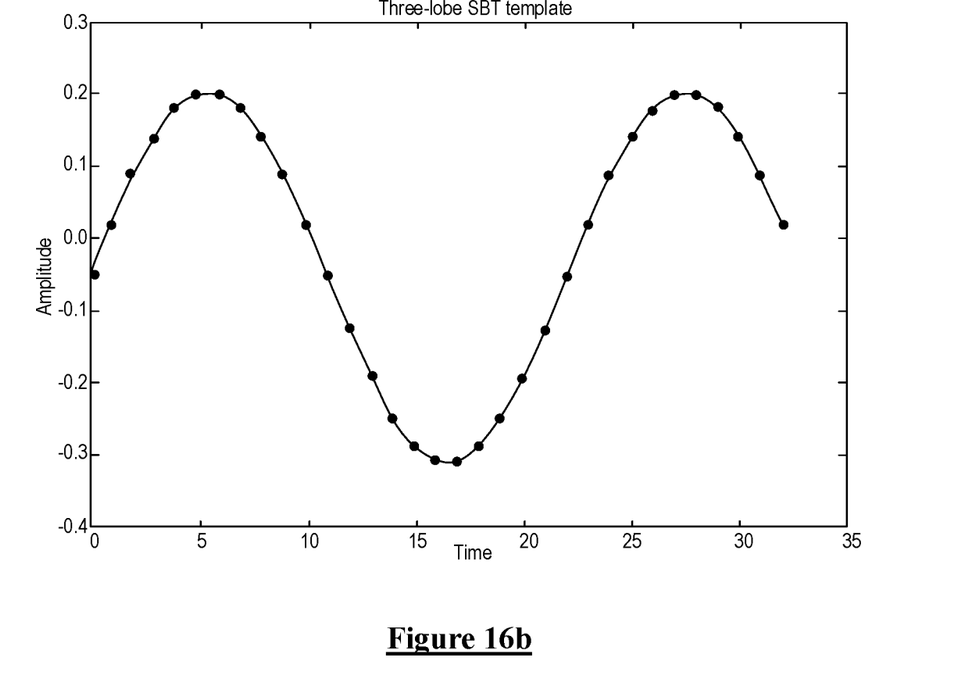

FIG. 16a illustrates the point values of a four lobed, 32 point filter template generated in accordance with the teachings of FIG. 15. FIG. 16b illustrates the point values of a three lobed, 33 point filter template generated in accordance with the teachings of FIG. 15 and in particular having a flat topped window.

It is further to be appreciated that cosine templates of 3, 5 or more lobes can be similarly generated, noting the FIG. 4 example for a four half cycles cosine template 402.

The preceding embodiments further describe a filter template built using a triangular window. The triangular window is superior to the Bartlett, Hanning, rectangular and the Kaiser-Bessel for a variety of beta values. The performance of the four-lobe triangular template can be within 2 dB of a matched filter for optimised offset. Nevertheless, alternative embodiments may utilise windows other than the triangular window to useful effect, and such embodiments are thus within the scope of the present invention.

Moreover, while the described embodiments use a single term of the SBT for response detection, the present invention further recognises that there are possible extensions to this method. Therefore, some embodiments of the invention may use multiple identical templates, but shifted in time. Even though these are not orthogonal, a successive approximation method creating a compound template may provide better approximation. Additionally or alternatively, some embodiments may use templates that are a sum of templates of different frequencies, templates of different offset and/or templates of different numbers of lobes.

A benefit of some embodiments of the present invention is that in some embodiments the detector produces an output based on a single neural measurement, without requiring multiple neural measurements to produce a detector output. Such embodiments may thus provide a swift response time of a feedback control loop utilising the detector output.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method for processing a neural measurement in order to determine a magnitude of a neural response in the neural measurement, the method comprising:

applying a first electrical stimulus to neural tissue of a patient, the first electrical stimulus defined by at least one stimulus parameter;

obtaining the neural measurement from one or more sense electrodes subsequent to the first electrical stimulus;

determining, based on the neural measurement, a time delay of a window to be applied to a subsequent neural measurement;

applying the window at the time delay to the subsequent neural measurement to produce a windowed neural measurement; and determining from the windowed neural measurement the magnitude of the neural response evoked by an electrical stimulus in the subsequent neural measurement.

2. The method of claim 1, wherein the determining the magnitude of the neural response comprises correlating the windowed neural measurement against a filter template.

3. The method of claim 2, wherein the filter template comprises at least three half cycles of an alternating waveform, amplitude modulated by a template window.

4. The method of claim 3 wherein the template window comprises a triangular window.

5. The method of claim 4 wherein the triangular window is a standard triangular window of length L comprising coefficients w(n) as follows:

For L odd:

$w(n)=2n/(L+1)$ for $1 \leq n \leq (L+1)/2 = 2-2n/(L+1)$ for $(L+1)/2+1 \leq n \leq L$ For L even:

$w(n)=(2n-1)/L$ for $1 \leq n \leq L/2 = 2-(2n-1)/L$ for $L/2+1 \leq n \leq L$.

6. The method of claim 4 wherein the triangular window is a Bartlett window of length L in which samples 1 and L are zero.

7. The method of claim 3 wherein the template window comprises one of a Hanning window, a rectangular window, and a Kaiser-Bessel window.

8. The method of claim 3 wherein the window comprises one or more basis functions derived from a sinusoidal binomial transform.

9. The method of claim 3 wherein the filter template comprises four half-cycles of an alternating waveform.

10. The method of claim 3 wherein the filter template comprises half cycles of a sine wave, amplitude modulated by the template window.

11. The method of claim 3 wherein the filter template comprises half cycles of a cosine wave, amplitude modulated by the template window.

12. The method of claim 2 wherein determining the magnitude comprises calculating only a single point of correlation.

13. The method of claim 2, wherein determining the time delay comprises:

applying the window at an approximate time delay to the neural measurement;

computing real and imaginary parts of the fundamental frequency of the discrete Fourier Transform (DFT) of the windowed neural measurement;

calculating a phase defined by the real and imaginary parts;

calculating, based on a fundamental frequency of the filter template, the time adjustment needed to change the calculated phase to $\pi/2$; and determining the time delay as the sum of the approximate time delay and the time adjustment.

14. The method of claim 1, wherein the time delay is re-determined prior to every processing of the neural measurement.

15. The method of claim 1, wherein the time delay is re-determined in response to a detected change in a posture of the patient.

16. The method of claim 1, further comprising using the magnitude of the neural response in a closed loop feedback circuit to determine the at least one stimulus parameter for a subsequent electrical stimulus.

17. An implantable device for processing a neural measurement in order to determine a magnitude of a neural response in the neural measurement, the device comprising:

an electrical stimulus source configured to generate a first electrical stimulus to be applied to neural tissue, the first electrical stimulus defined by at least one stimulus parameter;

measurement circuitry for obtaining the neural measurement from one or more sense electrodes subsequent to the first electrical stimulus; and a processor configured to:

determine, based on the neural measurement, a time delay of a window to be applied to a subsequent neural measurement;

apply the window at the time delay to the subsequent neural measurement to produce a windowed neural measurement; and determine from the windowed neural measurement the magnitude of the neural response evoked by the an electrical stimulus in the subsequent neural measurement.

* * * * *